(12) United States Patent
Ahmed

(10) Patent No.: US 7,025,740 B2
(45) Date of Patent: Apr. 11, 2006

(54) DEVICE FOR TREATING GLAUCOMA & METHOD OF MANUFACTURE

(76) Inventor: A. Mateen Ahmed, 10763 Edison Ct., Claremont, CA (US) 91730

( * ) Notice: Subject to any disclaimer, the term of this patent is extended or adjusted under 35 U.S.C. 154(b) by 372 days.

(21) Appl. No.: 10/420,077

(22) Filed: Apr. 22, 2003

(65) Prior Publication Data

US 2004/0215126 A1  Oct. 28, 2004

(51) Int. Cl.
*A61M 5/00* (2006.01)

(52) U.S. Cl. .............. 604/9; 604/8; 604/294; 606/4

(58) Field of Classification Search .............. 604/7–10, 604/264, 289, 294, 19; 606/4, 6, 107; 623/4.1, 623/6.64
See application file for complete search history.

(56) References Cited

U.S. PATENT DOCUMENTS

| | | | |
|---|---|---|---|
| 5,411,473 A * | 5/1995 | Ahmed | 604/8 |
| 5,476,445 A | 12/1995 | Baerveldt et al. | |
| 5,616,118 A * | 4/1997 | Ahmed | 604/8 |
| 5,681,275 A * | 10/1997 | Ahmed | 604/9 |
| 5,752,928 A * | 5/1998 | de Roulhac et al. | 604/8 |
| 5,785,674 A * | 7/1998 | Mateen | 604/9 |
| 6,007,510 A * | 12/1999 | Nigam | 604/8 |
| 6,193,682 B1 * | 2/2001 | Ahmed | 604/9 |
| 6,261,256 B1 * | 7/2001 | Ahmed | 604/9 |

\* cited by examiner

Primary Examiner—Patricia Bianco
Assistant Examiner—Leslie R. Deak
(74) Attorney, Agent, or Firm—John J. Connors; Connors & Assoc. Inc.

(57) ABSTRACT

A device implanted in an eye of a patient suffering from glaucoma includes a valve seated in a pocket of a plate. The pocket includes a flexible, resilient top wall forming at least a portion of a topside surface of the plate. A channel in communication with an outlet of the valve has a open top that allows aqueous humor flowing from the outlet of the valve to flow onto the topside surface of the plate.

30 Claims, 6 Drawing Sheets

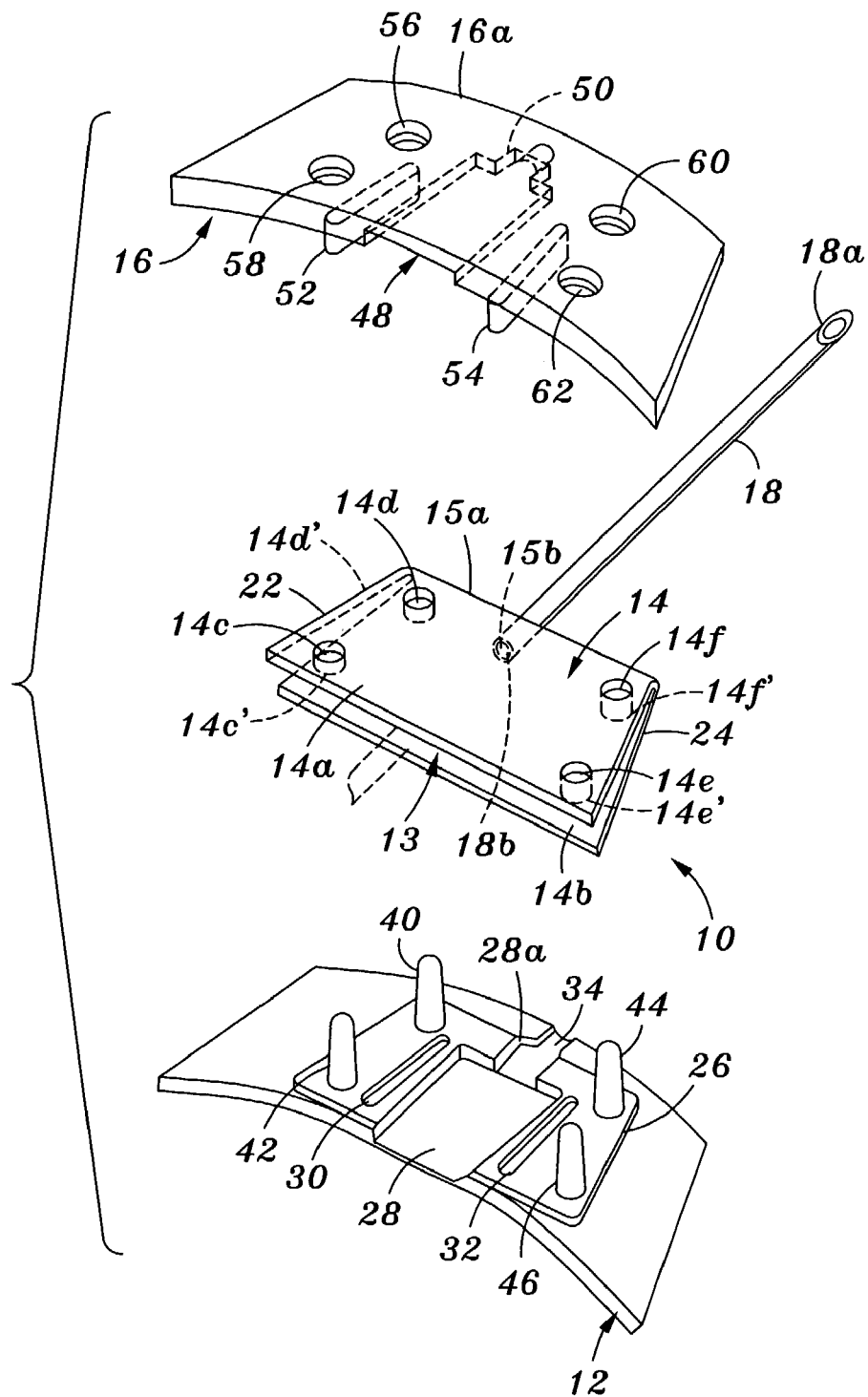

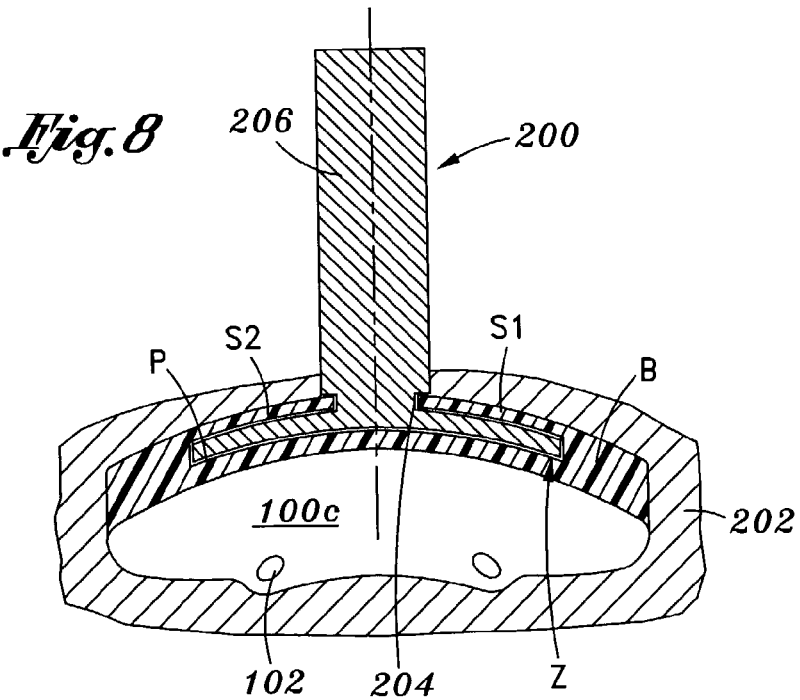
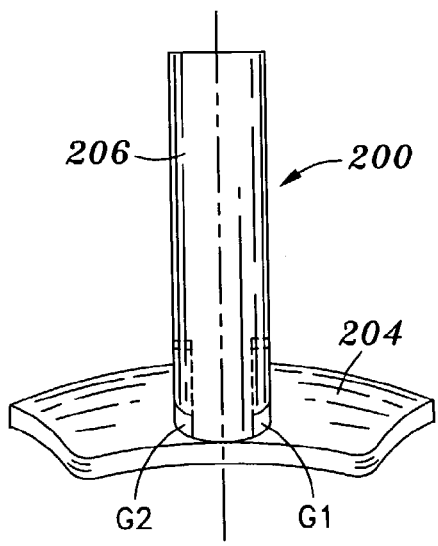
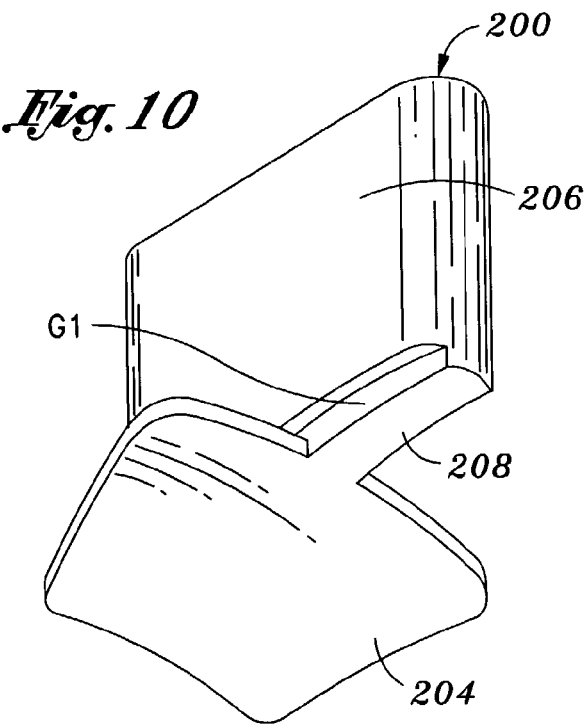

US 7,025,740 B2

DEVICE FOR TREATING GLAUCOMA & METHOD OF MANUFACTURE

INCORPORATION BY REFERENCE

Applicant incorporates herein by reference any and all U.S. patents, U.S. patent applications, and other documents cited or referred to in this application or cited or referred to in the U.S. patents and U.S. patent applications incorporated herein by reference.

DEFINITIONS

The words "comprising," "having," and "including," and other forms thereof, are intended to be equivalent in meaning and be open ended in that an item or items following any one of these words is not meant to be an exhaustive listing of such item or items, or meant to be limited to only the listed item or items.

BACKGROUND OF INVENTION

In U.S. Pat. No. 6,261,256 B1, the inventor discloses a pocket medical value for treating glaucoma. Although this pocket medical value is superior in many ways over the prior art, it would be desirable to improve both its design and method of manufacture to make it easier to make and use.

SUMMARY OF INVENTION

This invention has one or more features as discussed subsequently herein. After reading the following section entitled "DETAILED DESCRIPTION OF ONE EMBODIMENT OF THIS INVENTION," one will understand how the features of this invention provide its benefits. The benefits of this invention include, but are not limited to: lower production costs and improved ability to implant the device of this invention in the eye of a patient.

Without limiting the scope of this invention as expressed by the claims that follow, some, but not necessarily all, of its features are:

One, the device of this invention is useful in treating glaucoma. Typically, it has a substantially ovoid configuration and includes at least one orifice therein that enables the device to be sutured to the eye.

Two, the device includes a one way valve that opens and closes in response to intraocular pressure within an eye of a patient suffering from glaucoma. The valve has a valve body having a first end through which flows aqueous humor from an eye of a patient suffering from glaucoma upon implantation of the device into the eye. The valve body also has a second end opposed to the first end of the valve body to which one end of an inlet tube is attached. The inlet tube has a free end opposed to the one end of the inlet tube attached to the valve body. The free end is adapted to be inserted into an intraocular chamber of an eye of a patient suffering from glaucoma to enable the aqueous humor to flow from the intraocular chamber when the pressure with the intraocular chamber is at a predetermined level. The valve may include within the body an elastic membrane having overlying sections that form a normally closed slit in the first end of the valve from which the aqueous humor flows upon opening the slit.

Three, the device has a distribution plate made of a flexible, resilient material such as, for example, siliconized rubber. Usually, the plate has a thickness less than 0.07 inch and a surface area of at least 0.25 square inches to provide an excess portion that may be trimmed off to reduce the size of the device as desired. This distribution plate has a first end, a second end opposed to the first end, a substantially concave substantially smooth underside surface, and a substantially convex topside surface.

Four, the plate includes a pocket molded therein near the first end of the plate in which the valve is seated with the first end of the valve facing inward towards the second end of the plate. The valve and the pocket each may have substantially the same configuration so the valve fits snug within the pocket.

Five, the pocket includes a top wall forming at least a portion of the convex topside surface of the plate. This top wall is made of a flexible, resilient material and it has a first opening therein near the first end of the plate that provides access to enable the valve to be inserted into the pocket by manipulation of the flexible, resilient top wall. There is a recess at the first end of the plate adjacent the first opening into which a section of the first end of the inlet tube is seated upon insertion of the valve into the pocket. There is a second opening inward of the first opening that allows aqueous humor flowing from the first end of the valve to flow through the second opening onto the topside surface. The first and second openings usually are positioned along a longitudinal axis of the device.

Six, optionally the topside surface may have thereon at least two raised radial reinforcing members. The reinforcing members may straddle the second opening. The topside surface may be substantially smooth except for the reinforcing members, and it may include at least one drainage hole extending through the plate to allow the aqueous humor to flow over at least a portion of the topside surface through the drainage hole to the underside surface. The reinforcing members each have inner ends and outer ends, with the inner ends being closer to each other than the outer ends. This creates a reverse venturi effect to restrict flow of fluid from the outlet of the valve to thereby assist in creating a pool of fluid that tends to drain at least partially and slowly through the drainage hole.

Seven, the pocket has a channel extending therefrom inward towards the second end of the plate with the first opening overlying a central section of the pocket and the second opening overlying the channel. The first and second openings may be connected to form a unitary, elongated aperture in the topside surface. The aperture may extend lengthwise along the axis of the device.

These features are not listed in any rank order nor is this list intended to be exhaustive.

This invention also includes a method of manufacturing a medical device that includes a valve placed in a pocket in a body of the device. The valve has a predetermined overall configuration and the body has a predetermined overall configuration of greater volume than the valve. The method comprises:

providing a first mold having a cavity therein having a configuration substantially the same as the overall configuration of the body, providing a second mold adapted to be inserted into the cavity in the first mold to thereby provide a space between the assembled first and second molds, the second mold including an upright element and a tongue attached thereto having a predetermined configuration substantially the same as the configuration of the valve, inserting the second mold into the cavity in the first mold with the upright element projecting outward from the cavity to facilitate removal of the second mold from the first mold after formation of the body, the removal of the second mold forming an opening providing access to an interior of the pocket to enable the valve to be placed within the pocket, injecting a molten plastic into the space between the assembled first and second molds with the tongue forming the pocket in the body and upright element forming the opening in the pocket, the molten plastic upon solidification being resilient, after solidification of the plastic, separating the first and second molds, and placing the valve in the pocket by inserting the valve through the opening.

The pocket has a predetermined configuration that is deformed as the valve is placed therein and, due to the resiliency of the plastic, the pocket is restored to said predetermined configuration when the valve is placed therein. The tongue may have a substantially trapezoidal shaped. The upright element is at a right angle to the tongue.

DESCRIPTION OF DRAWINGS

One embodiment of this invention, illustrating all its features, will now be discussed in detail. This embodiment depicts the novel and non-obvious device of this invention for treating glaucoma as shown in the accompanying drawing, which is for illustrative purposes only. This drawing includes the following figures (Figs.), with like numerals indicating like parts:

FIG. 3 is an exploded perspective view of the valve shown in FIGS. 2 and 2A.

FIG. 8 is a cross-sectional view showing the body of the distribution plate being manufactured using an insert mold to form a pocket in the body of the plate.

FIG. 9 is an end view taken along line 9—9 of FIG. 12 of the insert mold shown in FIG. 8.

FIG. 10 is a perspective view of the insert mold shown in FIG. 9.

DETAILED DESCRIPTION OF ONE EMBODIMENT OF THIS INVENTION

Figure 1:
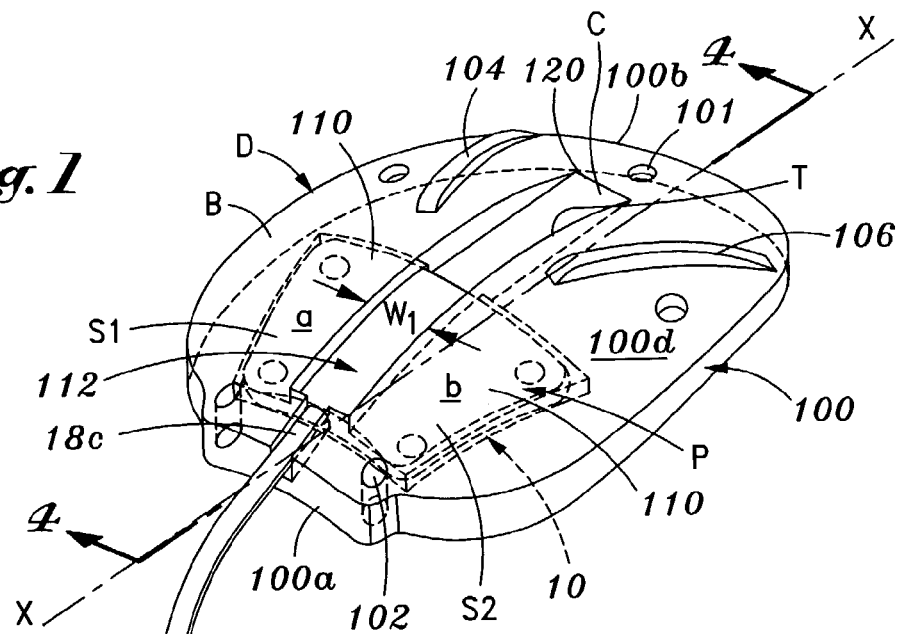
FIG. 1 is a perspective view of the device of this invention for treating glaucoma.

As depicted in FIG. 1, the device D of this invention for treating glaucoma includes a valve 10 seated within a pocket P of a distribution plate 100. In this embodiment, the device D has a substantially ovoid configuration and is symmetrical about its longitudinal axis X.

Figure 2:
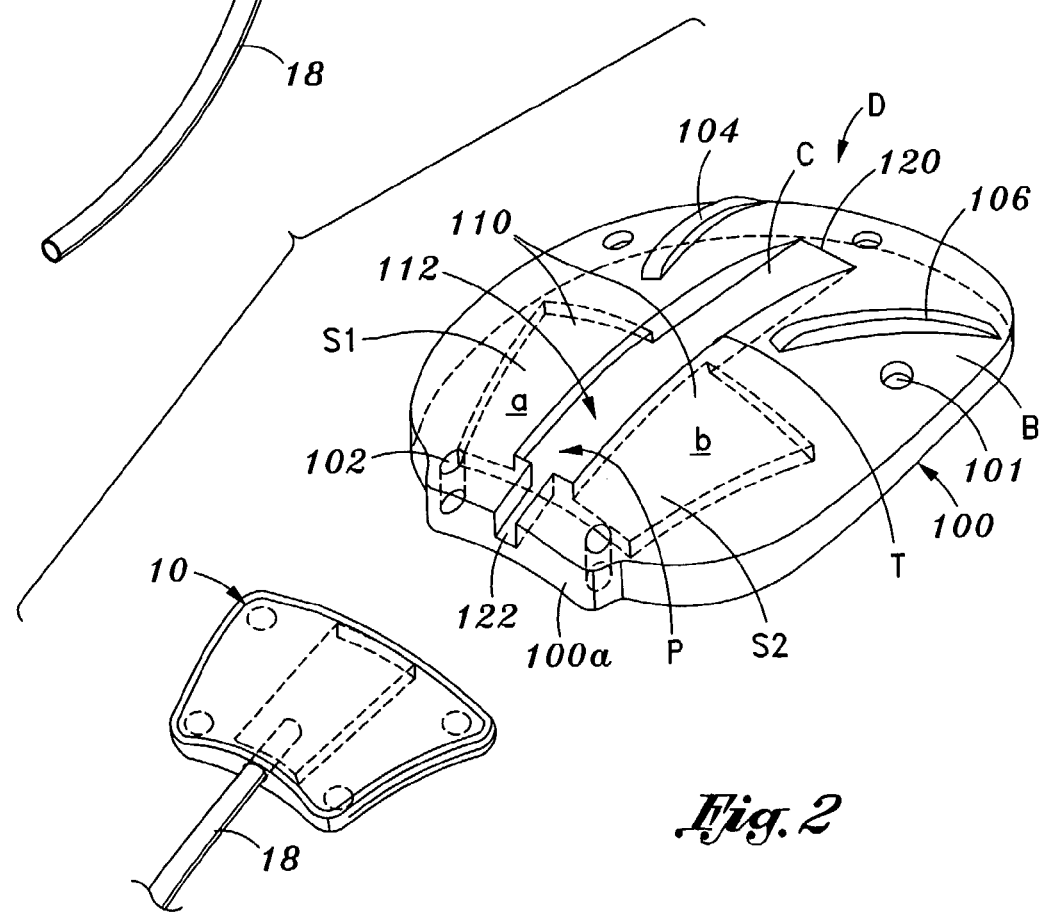
FIG. 2 is an exploded perspective view of the device of this invention for treating glaucoma.

FIG. 3 illustrates the valve 10 disclosed in U.S. Pat. No. 6,261,256 B1, which is an improvement in the valve disclosed in U.S. Pat. No. 5,071,408. It includes a bottom plate 12, a flexible, siliconized rubber membrane 14, a top plate 16, and a siliconized rubber inlet tube 18. The membrane 14 is folded to form a pair of essentially identically trapezoidal shaped membrane members 14a and 14b. The membrane members 14a and 14b are placed between aligned and spaced apart top plate 16 and bottom plate 12 as illustrated in FIG. 2b and these plates are pressed together and interlocked to hold the folded membrane 14 in position. Both the top and bottom plates 12 and 16 have segmented spherical shapes so that they conform to the curvature of the eyeball. Both plates 12 and 16 are made of a material that will not be rejected by the body. Suitable materials from which to make plates 12 and 16 are siliconized rubber, polypropylene, and polymethyl-methylacrelate (PMMA).

The membrane 14 is originally in a non-folded condition, and it has an hourglass-like shape narrowing at the central section 15a and then expanding outwardly therefrom in both directions. The membrane 14 has a thickness ranging between 0.004 and 0.007 inch. There is a central opening 15b in the member 14 and two sets of four spaced apart openings 14c, 14c', 14d, 14d', 14e, 14e', 14f, and 14f' along its opposed irregular sides 22 and 24. These holes 14c through 14f and 14c' through 14f' have a diameter of approximately 0.02 inch. Siliconized rubber is suitable for use as the membrane 14 and the inlet tube 18. One end 18b of the inlet tube 18 is inserted in central opening 15b. The inlet tube 18 extends from the membrane 14 so that a free end 18a may be surgically inserted into an intraocular chamber of the eye of a patient.

The bottom plate 12 has a generally trapezoidal-shaped configuration, with a raised four-sided central area 26, which includes therein a centrally located depression 28 of a generally trapezoidal configuration. On each side of this depression, running along substantially its entire length, are two grooves 30 and 32. At the one end 28a of the depression 28 is an indentation 34 that receives the tube 18. On the outside of each of the two grooves 30 and 32 are pairs of raised pins 40 and 42, and 44 and 46, respectively.

The top plate 16 is also a generally trapezoidal-shaped member having a centrally located generally trapezoidal shaped depression 48 on the bottom surface of this plate with an indentation 50 along its one side 16a. There are a pair of elongated finger elements 52 and 54 extending downwardly which interlock, respectively, in the grooves 30 and 32 in the bottom plate 12 when the two plates are pressed together. There are pairs of countersunk bores with 56 and 58, and 60 and 62, respectively, on the outside of each pair of finger elements 52 and 54, which receive the pairs of pins 40 and 42, and 44 and 46 in the bottom plate 12 when the top plate 16 and bottom plate are aligned and pressed together.

The inlet tube 18 is inserted into the central opening 15b and bonded to membrane 14. With the membrane 14 folded inwardly upon itself, it is placed between top plate 16 and bottom plate 12 and these plates are interconnected together, with the tube's outwardly extending section being placed between the indentations 34 and 50, respectively, in the plates 12 and 16. An adhesive is used to bond the end 18b of the tube 18 to the membrane 14. An example of a suitable adhesive is medical grade Silastic A, made by Dow Corning Corporation.

As depicted in FIG. 3, the overlapping membrane members 14a and 14b are held in position by pins 40, 42, 44, and 46 of bottom plate 12, which extend through openings 14c and 14c', 14d and 14d', 14e and 14e', and 14f and 14f' in the membrane and into bores 56, 58, 60, and 62 in the top plate 16 when the bottom plate 12 and top plate 16 are pressed together. This action also causes finger elements 52 and 54 extending from the bottom of top plate 16 to be wedged into grooves 30 and 32 of bottom plate 12. This causes the membrane 14 to stretch, placing it in tension so that a slit-like opening 13 is formed between the edges of the overlapping membrane members 14a and 14b. The trapezoidal depressions 28 and 48, respectively, in the bottom plate 12 and top plate 16, create a trapezoidal-shaped chamber 80 (FIG. 4) formed between the overlapping membrane members 14a and 14b. Aqueous humor from the patient's eye flows through the tube 18 into this trapezoidal-shaped chamber 80 and out the slit-like opening 13 when the pressure within the intraocular chamber of the patient's eye exceeds a predetermined level. Below this predetermined level, the tension within the membrane members 14a and 14b causes the slit-like opening 13 to close.

The distribution plate 100 (silicone plate) is solid piece of plastic made of a flexible, resilient material such as, for example, siliconized rubber. In this embodiment, the plate 100 has a thickness of about 0.058 inch and typically ranges in thickness from about 0.04 to about 0.07 inch. The valve 10 is even thinner than the plate 100. Such a thin plate 100 makes it easier for a surgeon to implant the device D into the eye of a patient and facilitates more rapid healing. There are orifices 102 near a proximal end 100a of the plate 100 that enables the device D to be sutured to a patient's eye with the free end 18a of the tube 18 inserted into the intraocular chamber of the patient's eye. The plate 100 includes near its distal end 100b drainage holes 101 extending through the plate to allow aqueous humor exiting the valve 10 to flow from its topside surface 100d to its underside surface 100c.

Figure 4:
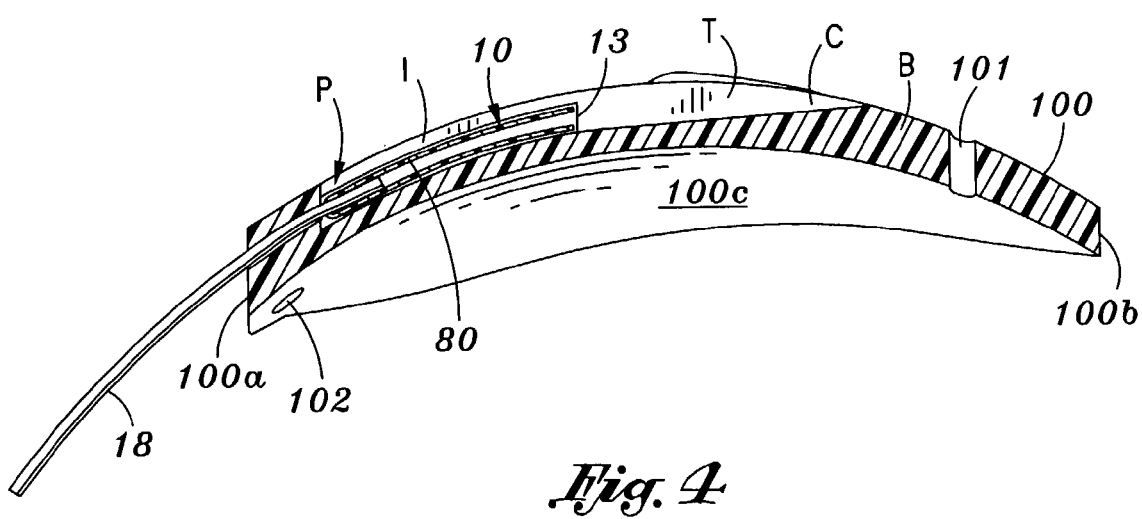
FIG. 4 is a cross-sectional view taken along line 4—4 of FIG. 1.
Figure 5:
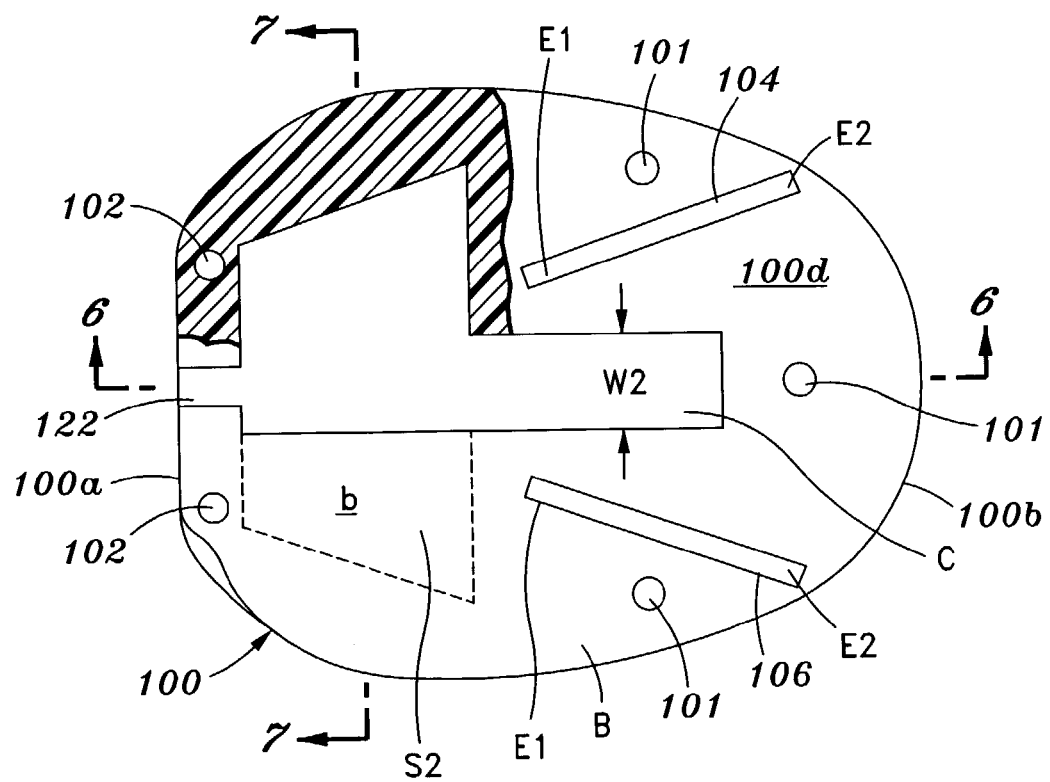
FIG. 5 is a plan view with sections broken away of the body of the distribution plate used with device of this invention for treating glaucoma.
Figure 6:
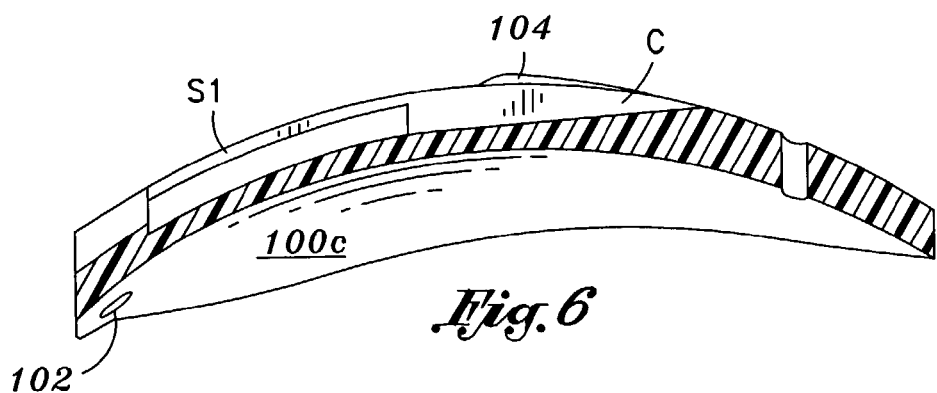
FIG. 6 is a cross-sectional view taken along line 6—6 of FIG. 5.
Figure 7:
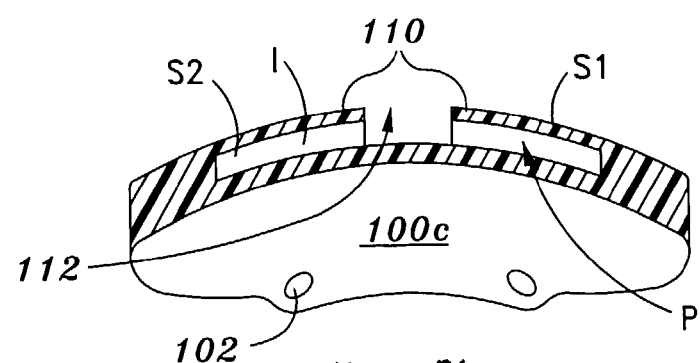
FIG. 7 is a cross-sectional view taken along line 7—7 of FIG. 5.
Figure 11:
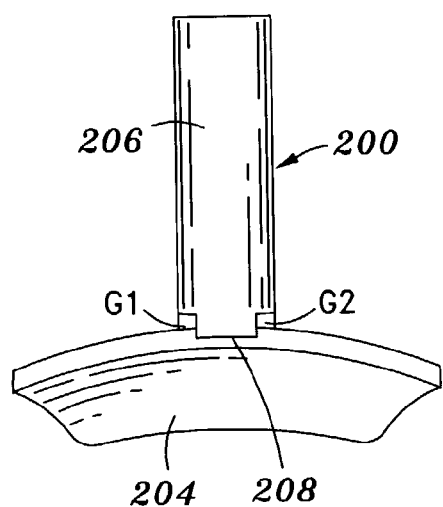
FIG. 11 is an end view taken along line 11—11 of FIG. 12 of the insert mold shown in FIG. 8.
Figure 12:
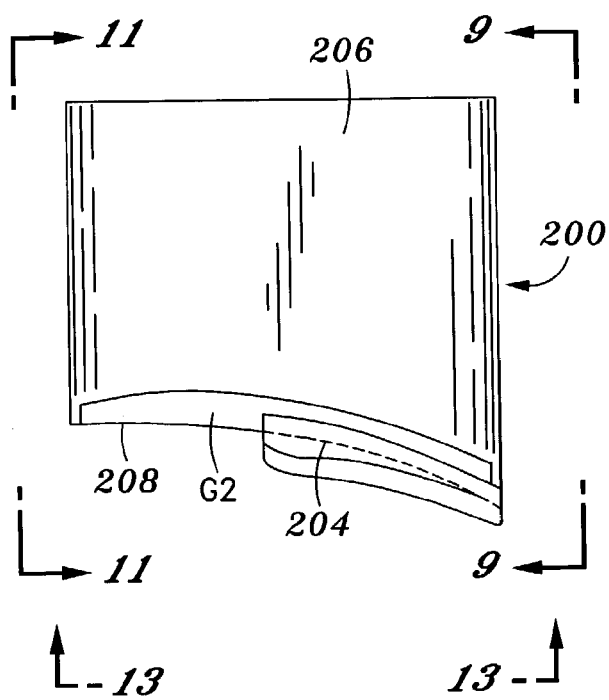
FIG. 12 is a side view of the insert mold shown in FIG. 8.
Figure 13:
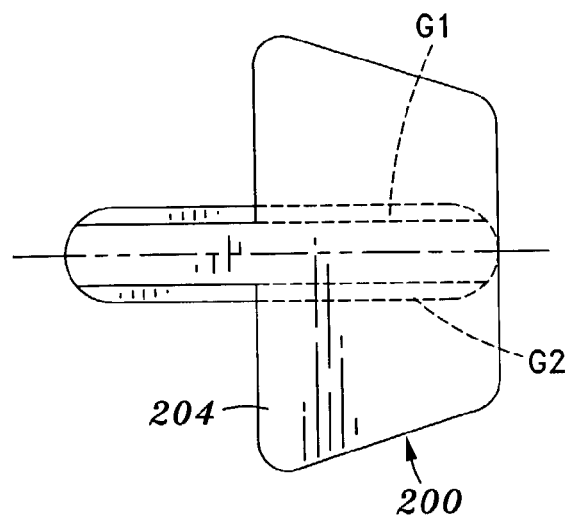
FIG. 13 is a bottom view taken along line 9—9 of FIG. 12 of the insert mold shown in FIG. 8.

As depicted in FIG. 5, a tapered distal end 100b of the distribution plate 100 is opposed to the proximal end 100a. This tapered distal end 100b is inserted into an incision made by the surgeon in the patient's eye ball. As best illustrated in FIGS. 4, 6 and 7, the plate's underside surface 100c is substantially concave and substantially smooth, being free of any structure that interferes with implantation of the device D. As best illustrated in FIGS. 1, 4 and 5, the plate's topside surface 100d is substantially convex and substantially smooth, including integral therewith a pair of raised, reinforcing members 104 and 106 on opposite sides of the longitudinal axis X. As discussed subsequently in greater detail, these reinforcing members 104 and 106 do not interfere with implantation of the device D. Because the topside surface 100d and underside surface 100c are substantially smooth, inserting the device D in the incision in the patient's eye is facilitated. There typically is a raised rim along the perimeter of the distribution plate of many prior art devices that impedes implantation of such devices. The plate 100 is free of any structure along its perimeter that could interfere with implanting the medical device D in a patient's eye.

The pocket P, which is near the proximal end 100a of the plate 100, is molded into the body B of the plate 100 using conventional insert molding techniques. The insert mold 200 used to form the pocket P is depicted in FIGS. 8 through 13. The valve 10 and pocket P each have substantially the same configuration so the valve fits snug within the pocket. In this embodiment they are both of a substantially trapezoidal configuration. The pocket P is covered by a top wall 10 comprising two spaced apart wall sections S1 and S2 that form between their inner edges an elongated opening 112 having a width $w_1$ from about 0.10 to about 0.125 inch. The opening 110 provides access to the interior I of the pocket P. Each section S1 and S2 has an exterior surface a and b, respectively, and these exterior surfaces a and b form at least a portion of the convex topside surface 100d of the plate 100 and are integral with this topside surface.

The pocket P has a recessed channel C within the body B of the plate 100 that extends from the pocket P towards the distal end 100b of the plate 100 and terminates at an outer end 120 that is set back from the distal end 100b and merges with the topside surface 10d. The channel C has an open top T having a width $w_2$ from about 0.35 to about 0.40 inch. To facilitate molding of the plate 100 it is best that the width $w_1$ and width $w_1$ are substantially equal. The opening 112 in the top wall 110 overlies a central section of the pocket P, and this opening and the open top T of the channel C both lie lengthwise along the axis X and form a unitary, elongated, rectangular aperture in the topside surface 100d.

Figure 2A:
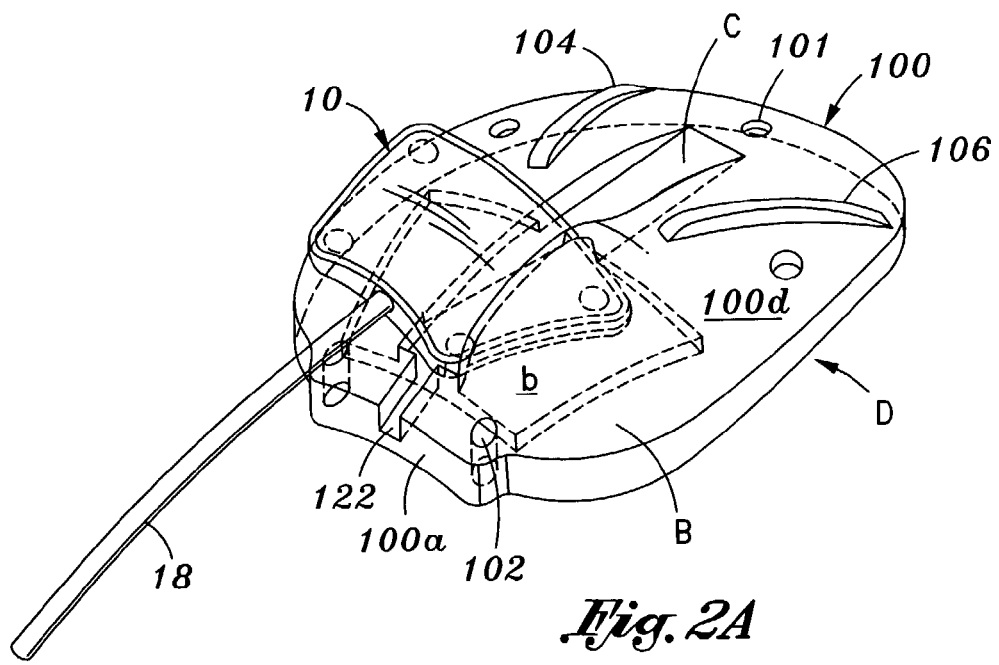
FIG. 2A is a perspective view showing a valve being inserted into a pocket in a distribution plate used in the device of this invention.

As shown in FIG. 2A, the valve 10 is manually positioned within the pocket P after formation of the plate 100 so that its slit-like opening 13 faces inward towards the distal end 100b of the plate 100. The opening 112 provides access for the valve 10 to enable the valve to be manually inserted into the pocket P by manipulation of the sections S1 and S2 of the top wall 110. Because these sections S1 and S2 of the top wall 110 are flexible and resilient, they stretch and elongate to spreading apart and expand the opening 112 adequately to enable insertion of the valve 10 into the pocket P. After insertion of the valve 10 into the pocket P, the sections S1 and S2 return to their un-stretched condition as shown in FIG. 1 due to the resiliency of the material from which they are made. As the valve is inserted into the pocket P, a portion 18c of the inlet tube 18 close to the membrane 14 is seated in a recess 122 at the proximal end 100a of the plate 100 adjacent the pocket P. The width of the recess 122 is slightly less than the diameter of the tube 18 so the tube fits snug within the recess without using an adhesive to hold the tube in position within the recess.

The reinforcing members 104 and 106 are sized and shaped so they do not materially interfere with implantation of the device D during surgery. They act as stiffeners that prevent the thin plate 100 from rolling up upon itself as the surgeon inserts the device D in the incision in the patent's eye. The reinforcing members 104 and 106 are straight elongated ridges having a width that does not exceed about 0.40 inch, typically being from about 0.35 to about 0.40 inch, a height that does not exceed about 0.06 inch, typically being from about 0.05 to about 0.06 inch, and a length does not exceed about 0.20 inch, typically being from about 0.15 to about 0.20 inch. And their outer ends E2 are each tapered. These reinforcing members 104 and 106 straddle the open top T of the channel C, with one reinforcing member 104 positioned on one side of the open top and the other reinforcing member 106 positioned on the other side of the open top. They diverge outward from the slit-like opening 13 of the valve 10 towards the distal end 100b of the plate 100 with their inner ends E1 being closer to each other and near the slit-like opening 13 of the valve 10 and their outer ends E2 being at a greater distance apart from each other than their inner ends.

When the valve 10 opens in response to the intraocular pressure reaching a predetermined level, aqueous humor flows from the slit-like opening 13 into the channel C, out the open top T and end 120, and then onto the topside surface 100d of the plate 100. Because of the diverging orientation of the reinforcing members 104 and 106, the rate of flow of the aqueous humor over the topside surface 100d is reduced, directing at least some of this slower moving aqueous humor to flow over the topside surface 100d then through the holes 101 to the underside surface 100c.

In accordance with one feature of this invention, the plate 100 is formed by insert molding, with the insert mold 200 being used to create the pocket P. As illustrated in FIG. 8, the mold 200 is placed in an opening (not shown) of an outer mould 202 to create a hollow zone Z in which molten plastic is injected between these molds. Both molds 200 and 202 are made of metal such as stainless steel. The mold 200 includes the curved trapezoidal shaped tongue 204 and an upright element 206 that is integral with the tongue and disposed along the longitudinal axis Y (FIG. 13) of the tongue at a right angle to the tongue. Where the tongue 204 and upright element 206 merge on each side of the upright element 206 are grooves G1 and G2. Between the grooves G1 and G2 and at the lower end of the upright element 206 is a rectangular shaped wedge 208. The tongue 204 and wedge 208 block the molten plastic from flowing into the space occupied by these components of the mold 200 to form in the plate 100, respectively, the pocket P and channel C. Upon cooling and solidification of the molten plastic, the mold 200 is pulled away from the solid plastic forming the body of the plate 100 through the opening 112 in the pocket and open top T channel and the plate is separated from the mold 202. Due to the resiliency of the material from which the plate 100 is made, it returns to the configuration shown in FIG. 5 upon removal of the insert mold 200.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention.

The invention claimed is:

1. A device for treating glaucoma comprising
a one way valve that opens and closes in response to intraocular pressure within an eye of a patient suffering from glaucoma, said valve including
a valve body having a first end through which flows aqueous humor from an eye of a patient suffering from glaucoma upon implantation of the device into the eye, and
a second end opposed to the first end of the valve body to which one end of an inlet tube is attached,
said inlet tube having a free end opposed to said one end of the inlet tube, said free end being adapted to be inserted into an intraocular chamber of a patient suffering from glaucoma to enable the aqueous humor to flow from the intraocular chamber when the pressure with the intraocular chamber is at a predetermined level, and
a distribution plate made of a flexible, resilient material and having a first end, a second end opposed to the first end, a substantially concave substantially smooth underside surface, a substantially convex topside surface,
said plate including a pocket molded therein near the first end of the plate in which the valve is seated with the first end of the valve facing inward towards the second end of the plate,
said pocket including a top wall forming at least a portion of the convex topside surface of the plate, said top wall having a first opening therein near the first end of the plate that provides access to enable the valve to be inserted into the pocket by manipulation of the top wall,
a recess at the first end of the plate adjacent the first opening into which a section of the first end of the inlet tube is seated upon insertion of the valve into the pocket, and
a second opening inward of the first opening that allows aqueous humor flowing from the first end of the valve to flow through the second opening onto the topside surface.

2. The device of claim 1 where said device has a substantially ovoid configuration.

3. The device of claim 1 where said flexible, resilient material is siliconized rubber.

4. The device of claim 1 where said plate has a thickness of less than 0.07 inch.

5. The device of claim 1 where said topside surface has thereon at least two raised radial reinforcing members.

6. The device of claim 5 where said reinforcing members straddle the second opening.

7. The device of claim 5 where said topside surface is substantially smooth except for the reinforcing members.

8. The device of claim 1 including at least one drainage hole extending through the plate to allow the aqueous humor to flow over at least a portion of the topside surface through said hole to the underside surface.

9. The device of claim 1 where the valve and the pocket each have substantially the same configuration so the valve fits snug within the pocket.

10. The device of claim 1 where the device has a longitudinal axis and the first and second openings are positioned along said axis.

11. The device of claim 10 where the pocket has a channel extending therefrom inward towards the second end of the plate with the first opening overlying a central section of the pocket and the second opening overlying the channel, said first and second openings being connected to form a unitary, elongated aperture in said topside surface.

12. The device of claim 1 where the device includes at least one orifice therein that enables the device to be sutured to the eye.

13. The device of claim 1 where the valve includes within the body an elastic membrane having overlying sections that form a normally closed slit in the first end of the valve from which the aqueous humor flows upon opening the slit.

14. A device for treating glaucoma comprising
a one way valve that opens and closes in response to intraocular pressure within an eye of a patient suffering from glaucoma,
said valve including an inlet tube having a one end attached to the valve and a free end adapted to be inserted into an intraocular chamber the eye to allow aqueous humor from the intraocular chamber to flow into the free end and through the valve when the intraocular pressure exceeds a predetermined level, a plate including a pocket with a channel extending therefrom, said pocket and valve having substantially the same configurations so the valve fits snug within the pocket, said pocket including a flexible, resilient top wall forming at least a portion of a topside surface of the plate, said top wall having an opening therein that enables the valve to be inserted into the pocket, said channel having a open top that allows aqueous humor flowing from the valve to flow onto the topside surface of the plate.

15. The device of claim 14 including a recess at an end of the plate into which a section of the one end of the inlet tube is seated snugly upon insertion of the valve into the pocket.

16. The device of claim 14 where the topside surface is substantially concave and substantially smooth, and the plate includes an underside surface that is substantially convex and substantially smooth.

17. The device of claim 14 where said device has a substantially ovoid configuration.

18. The device of claim 14 where said topside surface has thereon at least two raised radial reinforcing members.

19. The device of claim 18 where said reinforcing members straddle the open top of the channel.

20. The device of claim 18 including at least one drainage hole extending through the plate to allow the aqueous humor to flow over at least a portion of the topside surface through said hole to an underside surface.

21. The device of claim 14 where the opening in the top wall and the open top of the channel form a unitary, elongated aperture in said topside surface.

22. A device for treating glaucoma comprising
a one way valve including an inlet and outlet,
a body including plate and within the body a pocket in which the valve is seated,
a channel in the body in communication with the outlet of the valve,
said pocket including a flexible, resilient top wall forming at least a portion of a topside surface of the plate, said top wall having an opening therein that enables the valve to be inserted into the pocket, said channel having an open top that allows aqueous humor flowing from the outlet of the valve to flow onto the topside surface of the plate, said opening in the top wall and the open top of the channel forming a unitary, elongated aperture in said topside surface.

23. The device of claim 22 where the body has a longitudinal axis and is molded from a flexible, resilient material and the aperture extends lengthwise along said axis.

24. The device of claim 23 where the pocket and valve have substantially the same configurations so the valve fits snug within the pocket.

25. The device of claim 23 where said flexible, resilient material is siliconized rubber.

26. The device of claim 23 where said device has a substantially ovoid configuration.

27. The device of claim 23 where said body has a thickness less than 0.07 inch and a surface area of at least 0.25 square inches to provide an excess portion that may be trimmed off to reduce the size of the device as desired.

28. The device of claim 22 where said topside surface has thereon at least two raised radial reinforcing members that straddle the aperture.

29. The device of claim 28 including at least one drainage hole extending through the plate to allow the aqueous humor to flow over at least a portion of the topside surface through said drainage hole to the underside surface.

30. The device of claim 29 where reinforcing members each have inner ends and outer ends, said inner ends being closer to each other than the outer ends to create a reverse venturi effect to restrict flow of fluid from the outlet of the valve to thereby assist in creating a pool of fluid that trends to at least partially drain through the drainage hole.

* * * * *